(12) United States Patent
Mandro

(10) Patent No.: US 9,492,605 B2
(45) Date of Patent: *Nov. 15, 2016

(54) INFUSION PUMP ASSEMBLY WITH A BACKUP POWER SUPPLY

(71) Applicant: DEKA Products Limited Partnership, Manchester, NH (US)

(72) Inventor: Marc A. Mandro, Bow, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/181,170

(22) Filed: Feb. 14, 2014

(65) Prior Publication Data

US 2014/0163469 A1    Jun. 12, 2014

Related U.S. Application Data

(63) Continuation of application No. 13/305,004, filed on Nov. 28, 2011, now Pat. No. 8,684,972, which is a continuation of application No. 12/249,540, filed on Oct. 10, 2008, now Pat. No. 8,066,672.

(51) Int. Cl.
| | |
|---|---|
| *A61M 5/142* | (2006.01) |
| *A61M 5/145* | (2006.01) |
| *A61M 5/168* | (2006.01) |
| *H01M 10/42* | (2006.01) |
| *H01M 16/00* | (2006.01) |
| *A61M 5/50* | (2006.01) |

(52) U.S. Cl.
CPC ........... *A61M 5/142* (2013.01); *A61M 5/1452* (2013.01); *A61M 5/16854* (2013.01); *A61M 5/5086* (2013.01); *H01M 10/4264* (2013.01); *H01M 16/00* (2013.01); *A61M 2205/16* (2013.01); *A61M 2205/17* (2013.01); *A61M 2205/18* (2013.01); *A61M 2205/8206* (2013.01)

(58) Field of Classification Search
CPC ................... A61M 2205/16; A61M 2205/18; A61M 2205/17; A61M 2205/8206; A61M 5/142; A61M 5/14244
USPC .......................... 604/65–67, 131–155, 890.1
See application file for complete search history.

(56) References Cited

U.S. PATENT DOCUMENTS

| | | | |
|---|---|---|---|
| 3,623,474 A | 11/1971 | Heilman | |
| 4,503,494 A * | 3/1985 | Hamilton | G06F 1/00 365/229 |
| 4,693,684 A | 9/1987 | Blatherwick et al. | |
| 5,450,003 A * | 9/1995 | Cheon | 323/272 |
| 5,632,315 A | 5/1997 | Rose | |
| 5,800,387 A * | 9/1998 | Duffy et al. | 604/65 |
| 6,043,610 A | 3/2000 | Buell | |

(Continued)

*Primary Examiner* — Gerald Landry, II
(74) *Attorney, Agent, or Firm* — McCormick, Paulding & Huber LLP

(57) ABSTRACT

An infusion pump assembly includes a reservoir assembly configured to contain an infusible fluid. A motor assembly is configured to act upon the reservoir assembly and dispense at least a portion of the infusible fluid contained within the reservoir assembly. Processing logic is configured to control the motor assembly. A primary power supply is configured to provide primary electrical energy to at least a portion of the processing logic. A backup power supply is configured to provide backup electrical energy to the at least a portion of the processing logic in the event that the primary power supply fails to provide the primary electrical energy to the at least a portion of the processing logic.

25 Claims, 2 Drawing Sheets

(56) References Cited

U.S. PATENT DOCUMENTS

| | | | |
|---|---|---|---|
| 6,057,169 A * | 5/2000 | Singh | G06F 17/5068 257/E23.079 |
| 6,067,474 A * | 5/2000 | Schulman | A61N 1/08 607/33 |
| 6,146,109 A | 11/2000 | Davis et al. | |
| 6,611,410 B1 | 8/2003 | Makaran | |
| 7,039,755 B1 * | 5/2006 | Helms | G11C 11/406 365/222 |
| 7,113,821 B1 | 9/2006 | Sun et al. | |
| 8,108,040 B2 | 1/2012 | Bernard et al. | |
| 2002/0062086 A1 | 5/2002 | Miele et al. | |
| 2002/0161334 A1 | 10/2002 | Castellano et al. | |
| 2003/0074218 A1 | 4/2003 | Liff et al. | |
| 2007/0040449 A1 * | 2/2007 | Spurlin | A61M 5/1723 307/64 |
| 2007/0148014 A1 | 6/2007 | Anex et al. | |
| 2007/0149926 A1 | 6/2007 | Moberg et al. | |
| 2007/0215235 A1 | 9/2007 | Ranalletta et al. | |
| 2008/0051709 A1 | 2/2008 | Mounce et al. | |
| 2008/0125701 A1 * | 5/2008 | Moberg et al. | 604/67 |
| 2008/0269713 A1 | 10/2008 | Kavazov | |
| 2009/0062778 A1 * | 3/2009 | Bengtsson et al. | 604/890.1 |
| 2009/0139517 A1 | 6/2009 | Wachtel et al. | |
| 2009/0143732 A1 | 6/2009 | O'Connor et al. | |
| 2009/0172425 A1 * | 7/2009 | Cetin et al. | 713/300 |
| 2009/0198183 A1 | 8/2009 | Krumme et al. | |
| 2010/0022937 A1 * | 1/2010 | Bedingfield | A61M 1/16 604/6.09 |
| 2010/0022963 A1 * | 1/2010 | Edwards et al. | 604/197 |
| 2010/0080057 A1 * | 4/2010 | Reuter | G11C 5/143 365/185.04 |
| 2010/0094221 A1 | 4/2010 | Spencer et al. | |

\* cited by examiner

INFUSION PUMP ASSEMBLY WITH A BACKUP POWER SUPPLY

CROSS REFERENCE TO RELATED APPLICATIONS

This application is a continuation of U.S. application Ser. No. 13/305,004, filed on Nov. 28, 2011, which is a continuation of U.S. application Ser. No. 12/249,540, filed on Oct. 10, 2008, each of which applications is hereby incorporated herein by reference in its entirety.

TECHNICAL FIELD

This disclosure relates to infusion pump assemblies and, more particularly, to infusion pump assemblies that include redundant power supplies.

BACKGROUND

An infusion pump assembly may be used to infuse a fluid (e.g., a medication or nutrient) into a user. The fluid may be infused intravenously (i.e., into a vein), subcutaneously (i.e., into the skin), arterially (i.e., into an artery), and epidurally (i.e., into the epidural space).

Infusion pump assemblies may administer fluids in ways that would be impractically expensive/unreliable if performed manually by nursing staff. For example, an infusion pump assembly may repeatedly administer small quantities of an infusible fluid (e.g., 0.1 mL per hour), while allowing the user to request one-time larger "bolus" doses.

Unfortunately, the failure of the power supply included within the infusion pump assembly may result in the infusion pump assembly ceasing to operate. Further, as the infusion pump assembly is no longer operating, the user may not be warned of the failure of the infusion pump assembly.

SUMMARY OF DISCLOSURE

In a first implementation, an infusion pump assembly includes a reservoir assembly configured to contain an infusible fluid. A motor assembly is configured to act upon the reservoir assembly and dispense at least a portion of the infusible fluid contained within the reservoir assembly. Processing logic is configured to control the motor assembly. A primary power supply is configured to provide primary electrical energy to at least a portion of the processing logic. A backup power supply is configured to provide backup electrical energy to the at least a portion of the processing logic in the event that the primary power supply fails to provide the primary electrical energy to the at least a portion of the processing logic.

One or more of the following features may be included. The primary power supply may include a first battery. The backup power supply may be a super capacitor assembly.

The processing logic may include one or more circuit partitioning components configured to divide the processing logic into primary processing logic and backup processing logic. The primary processing logic may include a primary microprocessor. The backup processing logic may include a safety microprocessor. The one or more circuit partitioning components may include one or more of a diode assembly and a current limiting assembly.

The diode assembly may be configured to allow the primary power supply to charge the backup power supply while prohibiting the backup power supply from providing backup electrical energy to the primary processing logic in the event that the primary power supply fails to provide the primary electrical energy to the primary processing logic. The current limiting assembly may be configured to limit the amount of the primary electrical energy available to charge the backup power supply.

The primary power supply may be configured to provide electrical energy to one or more subsystems included within the infusion pump assembly. The primary power supply and the backup power supply may be configured to provide electrical energy to an audio system included within the infusion pump assembly. The audio system may be configured to provide an escalating alarm sequence in the event of a loss of a beacon signal. The escalating alarm sequence may include at least a low-intensity alarm and a high-intensity alarm.

In another implementation, an infusion pump assembly includes a reservoir assembly configured to contain an infusible fluid. A motor assembly is configured to act upon the reservoir assembly and dispense at least a portion of the infusible fluid contained within the reservoir assembly. Processing logic is configured to control the motor assembly. A first battery is configured to provide primary electrical energy to at least a portion of the processing logic. A super capacitor assembly is configured to provide backup electrical energy to the at least a portion of the processing logic in the event that the first battery fails to provide the primary electrical energy to the at least a portion of the processing logic.

One or more of the following features may be included. The processing logic may include one or more circuit partitioning components configured to divide the processing logic into primary processing logic and backup processing logic. The primary processing logic may include a primary microprocessor. The backup processing logic may include a safety microprocessor. The one or more circuit partitioning components may include one or more of a diode assembly and a current limiting assembly.

In another implementation, an infusion pump assembly includes a reservoir assembly configured to contain an infusible fluid. A motor assembly is configured to act upon the reservoir assembly and dispense at least a portion of the infusible fluid contained within the reservoir assembly. Processing logic is configured to control the motor assembly. A primary power supply is configured to provide primary electrical energy to at least a portion of the processing logic. A backup power supply is configured to provide backup electrical energy to the at least a portion of the processing logic in the event that the primary power supply fails to provide the primary electrical energy to the at least a portion of the processing logic. The processing logic includes one or more circuit partitioning components configured to divide the processing logic into primary processing logic and backup processing logic.

One or more of the following features may be included. The primary power supply may include a first battery. The backup power supply may be a super capacitor assembly. The primary processing logic may include a primary microprocessor. The backup processing logic may include a safety microprocessor.

The one or more circuit partitioning components may include one or more of a diode assembly and a current limiting assembly. The diode assembly may be configured to allow the primary power supply to charge the backup power supply while prohibiting the backup power supply from providing backup electrical energy to the primary processing logic in the event that the primary power supply fails to provide the primary electrical energy to the primary processing logic.

In another implementation, an alarm system includes processing logic configured to generate an alarm control signal. An RS232 line driver circuit is coupled to the processing logic and configured to receive the alarm control signal and generate an alarm output signal based, at least in part, upon the alarm control signal. An audio driver assembly is coupled to the RS232 line driver circuit and configured to receive the alarm output signal and generate an audible alarm signal based, at least in part, upon the alarm output signal.

One or more of the following features may be included. The audio driver assembly may include a Piezo electric diaphragm. The alarm system may be included within an infusion pump assembly. The infusion pump assembly may include a reservoir assembly configured to contain an infusible fluid. A motor assembly may be configured to act upon the reservoir assembly and dispense at least a portion of the infusible fluid contained within the reservoir assembly. A primary power supply may be configured to provide primary electrical energy to at least a portion of the processing logic. A backup power supply may be configured to provide backup electrical energy to the at least a portion of the processing logic in the event that the primary power supply fails to provide the primary electrical energy to the at least a portion of the processing logic. The processing logic may be further configured to control the motor assembly.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
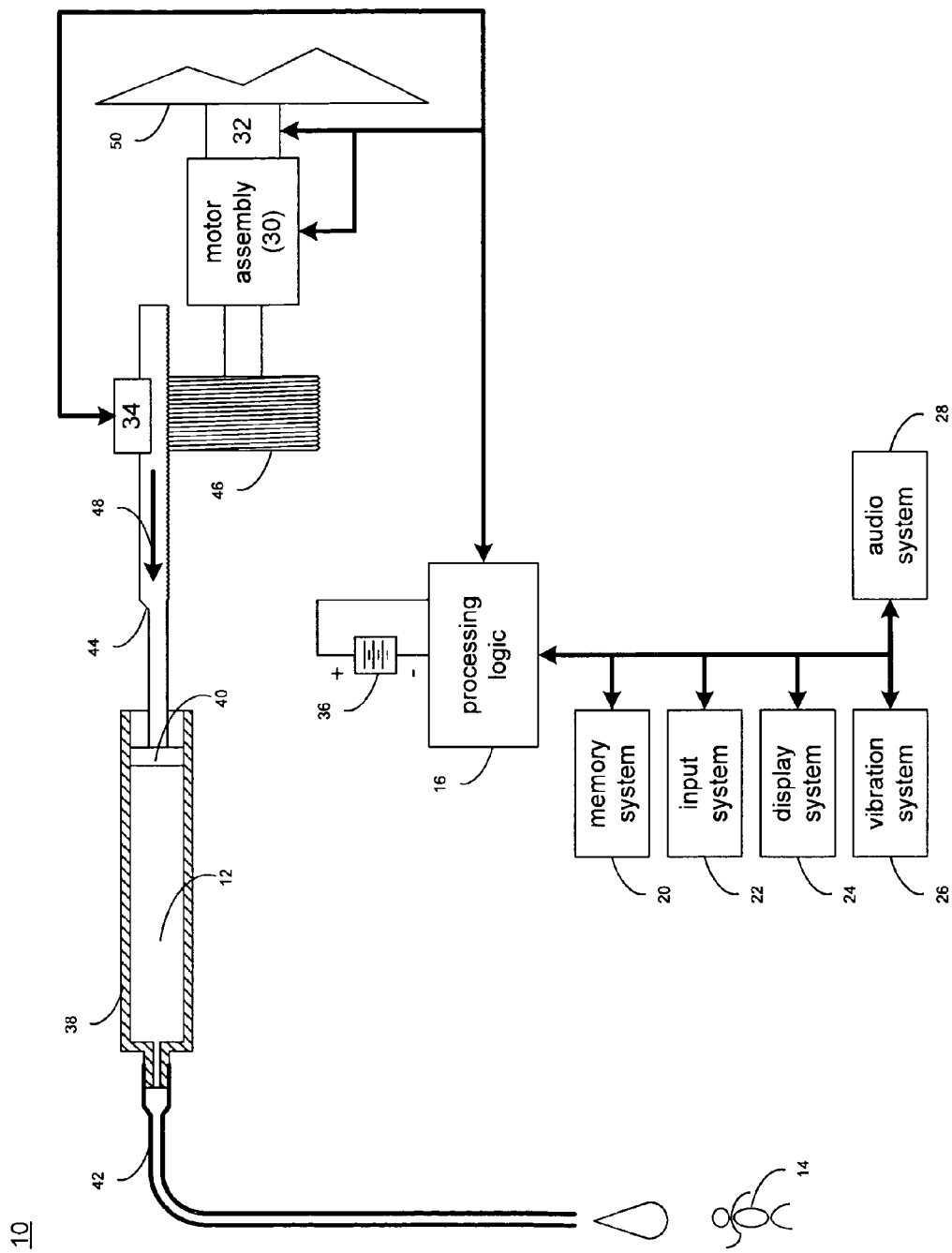
FIG. 1 is a diagrammatic view of an infusion pump assembly including processing logic.

Referring to FIG. 1, there is shown infusion pump assembly 10 that may be configured to deliver infusible fluid 12 to user 14. As discussed above, infusible fluid 12 may be delivered intravenously (i.e., into a vein), subcutaneously (i.e., into the skin), arterially (i.e., into an artery), and epidurally (i.e., into the epidural space). Examples of infusible fluid 12 may include but are not limited to insulin, nutrients, saline solution, antibiotics, analgesics, anesthetics, hormones, vasoactive drugs, and chelation drugs Infusion pump assembly 10 may include processing logic 16 that executes one or more processes that may be required for infusion pump assembly 10 to operate properly. Processing logic 16 may include one or more microprocessors (to be discussed below in greater detail), one or more input/output controllers (not shown), and cache memory devices (not shown). One or more data buses and/or memory buses may be used to interconnect processing logic 16 with one or more subsystems.

Examples of such subsystems may include but are not limited to memory system 20, input system 22, display system 24, vibration system 26, audio system 28, motor assembly 30, force sensor 32, and displacement detection device 34. Infusion pump assembly 10 may include primary power supply 36 (e.g. a first battery) for providing electrical power to at least a portion of processing logic 16 and one or more of the subsystems (e.g., memory system 20, input system 22, display system 24, vibration system 26, audio system 28, motor assembly 30, force sensor 32, and displacement detection device 34).

Infusion pump assembly 10 may include reservoir assembly 38 configured to contain infusible fluid 12. In some embodiments, reservoir assembly 38 may be a reservoir assembly similar to that described in U.S. Patent Application Publication No. US 2004-0135078-A1, published Jul. 15, 2004, which is herein incorporated by reference in its entirety. In other embodiments, the reservoir assembly may be any assembly in which fluid may be acted upon such that at least a portion of the fluid may flow out of the reservoir assembly, for example, the reservoir assembly, in various embodiments, may include, but is not limited to: a barrel with a plunger, a cassette or container at least partially constructed of a flexible membrane.

Plunger assembly 40 may be configured to displace infusible fluid 12 from reservoir assembly 38 through cannula assembly 42 so that infusible fluid 12 may be delivered to user 14. In this particular embodiment, plunger assembly 40 is shown to be displaceable by partial nut assembly 44, which may engage lead screw assembly 46 that may be rotatable by motor assembly 30 in response to signals received from processing logic 16. An example of partial nut assembly 44 may include but is not limited to a nut assembly that is configured to wrap around lead screw assembly 46 by e.g., 30 degrees. In some embodiments, the pump assembly may be similar to one described in U.S. Pat. No. 7,306,578, issued Dec. 11, 2007, which is herein incorporated by reference in its entirety. For example, in some embodiments, the infusion pump assembly 10 may include a housing that contains the components needed to cause the reservoir assembly 38 to deliver medication to a user, including the reservoir assembly 38, the motor assembly 30, processing logic 16, primary power supply 36 and backup power supply 108.

During operation of infusion pump assembly 10, infusible fluid 12 may be delivered to user 14 in accordance with e.g. a defined delivery schedule. For illustrative purposes only, assume that infusion pump assembly 10 is configured to provide 0.00025 mL of infusible fluid 12 to user 14 every three minutes. Accordingly, every three minutes, processing logic 16 may provide power to motor assembly 30 to allow motor assembly 30 to rotate lead screw assembly 46 the appropriate amount so that partial nut assembly 44 (and therefore plunger assembly 40) may be displaced the appropriate amount in the direction of arrow 48 so that 0.00025 mL of infusible fluid 12 are provided to user 14 (via cannula 42). It should be understood that the volume of infusible fluid 12 that may be provided to user 14 may vary based upon, at least in part, the nature of the infusible fluid (e.g., the type of fluid, concentration, etc.), use parameters (e.g., treatment type, dosage, etc.), as well as various other factors that will be understood by one having skill in the art. As such, the foregoing illustrative example should not be construed as a limitation of the present disclosure.

Force sensor 32 may be configured to provide processing logic 16 with data concerning the force required to drive plunger assembly 40 into reservoir assembly 38. Force sensor 32 may include one or more strain gauges and/or pressure sensing gauges and may be positioned between motor assembly 30 and an immovable object (e.g. bracket assembly 50) included within infusion pump assembly 10.

In one embodiment, force sensor 32 includes four strain gauges (not shown), such that: two of the four strain gauges are configured to be compressed when driving plunger 40 into reservoir assembly 38; and two of the four strain gauges are configured to be stretched when driving plunger 40 into reservoir assembly 38. The four strain gauges (not shown) may be connected to a Wheatstone Bridge (not shown) that produces an analog force signal (not shown) that is a function of the pressure sensed by force sensor 32. The analog force signal (not shown) produced by force sensor 32 may be provided to an analog-to-digital converter (not shown) that may convert the analog force signal (not shown) into a digital force signal (not shown) that may be provided to processing logic 16. An amplifier assembly (not shown) may be positioned prior to the above-described analog-to-digital converter and may be configured to amplify the output of e.g., force sensor 32 to a level sufficient to be processed by the above-described analog-to-digital converter.

Motor assembly 30 may be configured as e.g., a brush-type DC electric motor. Further, motor assembly 30 may include a reduction gear assembly (not shown) that e.g. requires motor assembly 30 to rotate e.g., three-thousand revolutions for each revolution of lead screw assembly 42, thus increasing the torque and resolution of motor assembly 30 by a factor of three-thousand.

Figure 2:
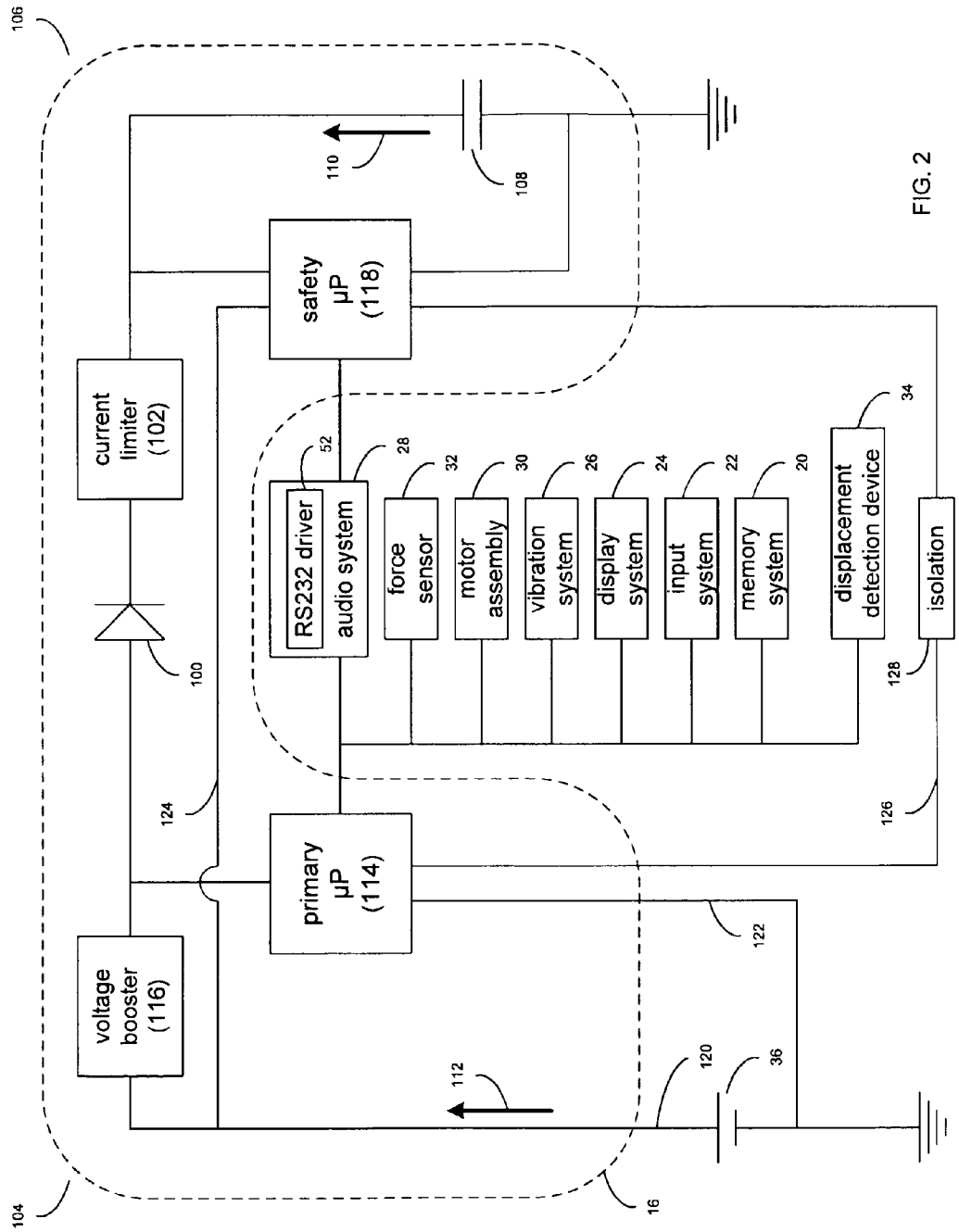
FIG. 2 is a more-detailed diagrammatic view of the processing logic of FIG. 1.

Referring also to FIG. 2, there is shown a more-detailed diagrammatic view of processing logic 16. Processing logic 16 may include one or more circuit partitioning components 100, 102 configured to divide processing logic 16 into primary processing logic 104 and backup processing logic 106. Examples of one or more circuit partitioning components 100, 102 may include but are not limited to diode assembly 100 and current limiting assembly 102.

Diode assembly 100 may be configured to allow primary power supply 36 to charge backup power supply 108 included within backup processing logic 106, while prohibiting backup power supply 108 from providing backup electrical energy 110 to primary processing logic 104 in the event that some form of failure prevents primary power supply 36 from providing primary electrical energy 112 to primary processing logic 104. An example of backup power supply 108 may include but is not limited to a super capacitor assembly. An example of such a super capacitor assembly may include but is not limited to a electric double-layer capacitor manufactured by Elna Co. Ltd. of Yokohama, Japan.

Current limiting assembly 102 may be configured to limit the amount of primary electrical energy 112 available to charge backup power supply 108. Specifically, as primary power supply 36 may be configured to charge backup power supply 108, the amount of current available from primary power supply 36 may be limited to e.g., avoid depriving primary processing logic 104 of a requisite portion of primary electrical energy 112.

Primary processing logic 104 may include primary microprocessor 114 and voltage booster circuit 116. An example of primary microprocessor 114 may include but is not limited to a H8S/2000 manufactured by Renesas Technology America Inc. of San Jose, Calif. Voltage booster circuit 116 may be configured to increase the voltage potential of primary electrical energy 112 provided by primary power supply 36 to a level sufficient to power primary microprocessor 114. An example of voltage booster circuit 116 may include but is not limited to a LTC3421 manufactured by Linear Technology of Milpitas, Calif.

Current limiting assembly 102 may be configured to limit the amount of current available to charge backup power supply 108 during the power-up of primary microprocessor 114. Specifically and for illustrative purposes, current limiter assembly 102 may be controlled by primary microprocessor 114 and current limiting assembly 102 may be disabled (i.e., provide no charging current to backup power supply 108) until after primary microprocessor 114 is fully powered up. Upon primary microprocessor 114 being fully powered up, primary microprocessor 114 may now enable current limiting assembly 102, thus providing charging current to backup power supply 108. Alternatively and upon being initially energized, current limiting assembly 102 may be configured to prohibit the flow of charging current to backup power supply 108 for a time sufficient to allow for the powering up of primary microprocessor 114.

Backup processing logic 106 may include backup power supply 108 and safety microprocessor 118. An example of safety microprocessor 118 may include but is not limited to a MSP430 manufactured by Texas Instruments of Dallas, Tex.

Primary power supply 36 may be configured to provide primary electrical energy 112 to at least a portion of processing logic 16. Specifically and during normal operation of infusion pump assembly 10, primary power supply 36 may be configured to provide primary electrical energy 112 to all of processing logic 16 (including the various components of primary processing logic 104 and backup processing logic 106), as well as various subsystems included within infusion pump assembly 10.

Examples of such subsystems may include but are not limited to memory system 20, input system 22, display system 24, vibration system 26, audio system 28, motor assembly 30, force sensor 32, and displacement detection device 34.

Backup power supply 108 may be configured to provide backup electrical energy 110 to the at least a portion of processing logic 16 in the event that primary power supply 36 fails to provide primary electrical energy 112 to at least a portion of processing logic 16. Specifically, in the event that primary power supply 36 fails and, therefore, can no longer provide primary electrical energy 112 to processing logic 16, backup power supply 108 may be configured to provide backup electrical energy 110 to backup processing logic 106.

For illustrative purposes only, assume that infusion pump assembly 10 is operating normally and primary power supply 36 is providing primary electrical energy 112 to processing logic 16. As discussed above, voltage booster circuit 116 may increase the voltage potential of primary electrical energy 112 to a level sufficient to power primary microprocessor 114, wherein voltage booster circuit 116 and primary microprocessor 114 are both included within primary processing logic 104.

Further, diode assembly 100 may allow a portion of primary electrical energy 112 to enter backup processing logic 106, thus enabling the operation of safety microprocessor 118 and the charging of backup power supply 108. As discussed above an example of backup power supply 108 may include but is not limited to a super capacitor. As discussed above, current limiter assembly 102 may limit the quantity of current provided by primary power supply 36 to backup processing logic 106, thus preventing the diversion of too large a portion of primary electrical energy 112 from primary processing logic 104 to backup processing logic 106.

Accordingly, in addition to powering safety microprocessor 118, primary power supply 36 may charge backup power supply 108. In a preferred embodiment, backup power supply 108 is a 0.33 farad super capacitor.

Safety microprocessor 118 may monitor the status of primary power supply 36 by monitoring the voltage potential present at the input of voltage booster circuit 116. Alternatively, safety microprocessor 118 may monitor the status of primary power supply 36 by e.g. monitoring (via conductor 124) the voltage potential present at the output of voltage booster circuit 116. Further still, safety microprocessor 118 and primary microprocessor 114 may be electrically-coupled via e.g. conductor 126 and primary microprocessor 114 may be configured to continuously provide a "beacon" signal to safety microprocessor 118. Conductor 126 may include isolation circuit 128 (e.g., one or more diodes assemblies) to electrically isolate safety microprocessor 118 and primary microprocessor 114. Accordingly, provided safety microprocessor 118 continues to receive the "beacon" signal from primary microprocessor 114, primary microprocessor 114 is functioning and, therefore, being properly powered by primary power supply 36. In the event that safety microprocessor 118 fails to receive the "beacon" signal from primary microprocessor 114, an alarm sequence may be initiated.

Further still, safety microprocessor 118 may be configured to continuously provide a "beacon" signal to primary microprocessor 114. Accordingly, provided primary microprocessor 114 continues to receive the "beacon" signal from safety microprocessor 118, safety microprocessor 118 is functioning and, therefore, being properly powered by backup power supply 108. In the event that primary microprocessor 114 fails to receive the "beacon" signal from safety microprocessor 118, an alarm sequence may be initiated.

As used in this disclosure, a "beacon" signal may be considered an event that is performed by primary microprocessor 114 (and/or safety microprocessor 118) solely for the purpose of making the presence of primary microprocessor 114 (and/or safety microprocessor 118) known. Additionally/alternatively, the "beacon" signal may be considered an event that is performed by primary microprocessor 114 (and/or safety microprocessor 118) for the purpose of performing a task, wherein the execution of this event is monitored by safety microprocessor 118 (and/or primary microprocessor 114) to confirm the presence of primary microprocessor 114 (and/or safety microprocessor 118).

Assume for illustrative purposes that primary power supply 36 fails. For example, assume that primary power supply 36 physically fails (as opposed to simply becoming discharged). Examples of such a failure may include but are not limited to the failing of a cell (not shown) within primary power supply 36 and the failing of a conductor (e.g., one or more of conductors 120, 122) that electrically-couples primary power supply 36 to processing logic 16. Accordingly, in the event of such a failure, primary power supply 36 may no longer provide primary electrical energy 112 to processing logic 16.

However, when such a failure of primary power supply 36 occurs, the voltage potential present at the output of voltage booster circuit 116 and the voltage potential present at the input of voltage booster circuit 116 may be reduced to zero. Since safety microprocessor 118 may monitor (as discussed above) one or more of these voltage potentials, safety microprocessor 118 may be knowledgeable that primary power supply 36 has failed.

Further, when such a failure of primary power supply 36 occurs, primary microprocessor 114 will no longer be powered and, therefore, primary microprocessor 114 will no longer produce the above-described "beacon" signals. Since safety microprocessor 118 monitors the above-described "beacon" signals, safety microprocessor 118 may be knowledgeable that primary power supply 36 has failed.

As discussed above, in the event of such a failure of primary power supply 36, as diode assembly 100 is reversed-biased, backup power supply 108 may not provide backup electrical energy 110 to primary processing logic 104. Accordingly, primary processing logic 104 will know longer function.

Upon sensing the failure of primary power supply 36, safety microprocessor 118 may initiate an alarm sequence that may result in audio system 28 being energized. Audio system 28 may be controllable by both safety microprocessor 118 and primary microprocessor 114. Alternatively, a separate audio system may be used for each of safety microprocessor 118 and primary microprocessor 114. Audio system 28 may include a Piezo electric diaphragm, an example of which may include but is not limited to a 7BB-15-6 manufactured by Murata of Kyoto, Japan Audio system 28 may further include an RS232 line driver circuit 52, such as a MAX3319/MAX3221 manufactured by Maxim Integrated Products of Sunnyvale, Calif. One or more of primary microprocessor 114 and safety microprocessor 118 may be configured to provide an alarm control signal (e.g., a square wave; not shown) to RS232 line driver circuit 52 to generate an alarm output signal (not shown) that may be provided to and may drive the above-described Piezo electric diaphragm.

The alarm sequence initiated by safety microprocessor 118 is intended to inform user 14 of the failure of primary power supply 36 so that user 14 may take the appropriate action (e.g. seeking an alternative means to have their therapy performed and/or having infusion pump assembly 10 repaired/replaced). Backup power supply 108 may be sized so that safety microprocessor 118 and audio system 28 may continue to function for up to fifteen minutes or more after the failure of primary power supply 36 (i.e., depending on design specifications).

The alarm sequence initiated by safety microprocessor 118 and/or primary microprocessor 114 may be an "escalating" alarm sequence in some embodiments. For example, at first a discreet "vibrating" alarm may be initiated (via vibration system 26). In the event that this "vibrating" alarm is not acknowledged within a defined period of time (e.g., one minute), a low volume audible alarm may be initiated. In the event that this low volume alarm is not acknowledged within a defined period of time (e.g., one minute), a medium volume audible alarm may be initiated. In the event that this medium volume alarm is not acknowledged within a defined period of time (e.g., one minute), a high volume audible alarm may be initiated. The escalating alarm sequence may provide a notification to user 14, in which the notification may be discrete or less disruptive at the onset. The initially discreet or less disruptive notification may be advantageous as user 14 may experience minimal disruption. However, in the event that user 14 does not acknowledge the alarm, the escalating nature of the alarm may provide for additional layers of safety to user 14. Additionally, in a case of audio system 28 error, or vibration system 26 error, the escalating alarm sequence, which may include both vibration and audio alarms, may insure that user 14 may be notified regardless of whether both systems 26, 28 are functioning.

Audio system 28, in some embodiments, may be configured to perform a self test upon power up. For example, upon infusion pump assembly 10 being initially powered up, audio system 28 may provide a "beep-type" signal to each sound generating device included within audio system 28. In the event that user 14 does not hear these "beep-type" signal(s), user 14 may take the appropriate action (e.g. seeking an alternative means to have their therapy performed and/or having infusion pump assembly 10 repaired/replaced). As discussed above, audio system 28 may be controllable by safety microprocessor 118 and/or primary micro-processor 114. Accordingly, when performing the above-described self test upon power up, safety microprocessor 118 and/or primary microprocessor 114 may control the above-described self test. This feature may provide for additional safety to user 14, as user 14 may be alerted to a system error earlier than may otherwise be the case. Thus, a method may be provided to notify the user early of system errors. Also, the system may otherwise not be aware of an error in audio system 28, thus, this feature provides for identification of a failure by user 14 that may otherwise go undetected.

During the failure of primary power supply 36, safety microprocessor 118 may continue to monitor the voltage potential present at the output of voltage booster circuit 116 and/or the voltage potential present at the input of voltage booster circuit 116. Additionally, safety microprocessor 118 may continue to monitor for the presence of the above-described "beacon" signals. Accordingly, in the event that the failure of primary power supply 36 was a temporary event (e.g. primary power supply 36 is an out-of-date battery and is being replaced with a new battery), safety microprocessor 118 may be knowledgeable when primary power supply 36 is once again functioning properly.

Upon primary power supply 36 once again functioning properly, diode assembly 100 and current limiting assembly 102 may allow a portion of primary electrical energy 112 produced by primary power supply 36 to recharge backup power supply 108.

Additionally, safety microprocessor 118 and primary microprocessor 114 may each maintain a real-time clock, so that the various doses of infusible fluid may be dispensed at the appropriate time of day. As primary microprocessor 114 was not functioning during the failure of primary power supply 36, the real-time clock maintained within primary microprocessor 114 may no longer be accurate. Accordingly, the real-time clock maintained within safety microprocessor 118 may be used to reset the real-time clock maintained within primary microprocessor 114.

A number of implementations have been described. Nevertheless, it will be understood that various modifications may be made. Accordingly, other implementations are within the scope of the following claims.

What is claimed is:

1. An infusion pump assembly comprising:
   a reservoir assembly configured to contain an infusible fluid;
   a motor assembly configured to dispense infusible fluid from the reservoir assembly;
   processing logic configured to control the motor assembly, the processing logic including one or more circuit partitioning components configured to divide the processing logic into primary processing logic and backup processing logic;
   a primary power supply configured to provide primary electrical energy to at least a portion of the processing logic including the backup processing logic; and
   a backup power supply configured to provide backup electrical energy to the backup processing logic in the event that the primary power supply fails to provide the primary electrical energy to the at least a portion of the processing logic.

2. The infusion pump assembly of claim 1 wherein the primary power supply includes a first battery.

3. The infusion pump assembly of claim 1 wherein the backup power supply is a super capacitor assembly.

4. The infusion pump assembly of claim 1 wherein the primary processing logic includes a primary microprocessor.

5. The infusion pump assembly of claim 1 wherein the backup processing logic includes a safety microprocessor.

6. The infusion pump assembly of claim 1 wherein the one or more circuit partitioning components includes one or more of a diode assembly and a current limiting assembly.

7. The infusion pump assembly of claim 6 wherein the diode assembly is configured to allow the primary power supply to charge the backup power supply while prohibiting the backup power supply from providing backup electrical energy to the primary processing logic in the event that the primary power supply fails to provide the primary electrical energy to the primary processing logic.

8. The infusion pump assembly of claim 6 wherein the current limiting assembly is configured to limit the amount of the primary electrical energy available to charge the backup power supply.

9. The infusion pump assembly of claim 1 wherein the primary power supply is configured to provide electrical energy to one or more subsystems included within the infusion pump assembly.

10. The infusion pump assembly of claim 1 wherein the primary power supply and the backup power supply are configured to provide electrical energy to an audio system included within the infusion pump assembly.

11. The infusion pump assembly of claim 10 wherein the audio system is configured to provide an escalating alarm sequence in the event of a loss of a beacon signal, wherein the escalating alarm sequence includes at least a low-intensity alarm and a high-intensity alarm.

12. The infusion pump assembly of claim 1 wherein the processing logic includes one or more circuit partitioning components configured to allow the primary power supply to charge the backup power supply by diverting a portion of the primary electrical energy from the at least a portion of the processing logic to the backup power supply.

13. An infusion pump assembly comprising:
   a reservoir assembly configured to contain an infusible fluid;
   a motor assembly configured to dispense at least a portion of the infusible fluid contained within the reservoir assembly;
   processing logic configured to control the motor assembly;
   one or more circuit partitioning components configured to divide the processing logic into primary processing logic and backup processing logic;
   a first battery configured to provide primary electrical energy to at least a portion of the processing logic; and
   a super capacitor assembly configured to provide backup electrical energy to the at least a portion of the processing logic in the event that the first battery fails to provide the primary electrical energy to the at least a portion of the processing logic during operation of the infusion pump assembly.

14. The infusion pump assembly of claim 13 wherein the primary processing logic includes a primary microprocessor.

15. The infusion pump assembly of claim 13 wherein the backup processing logic includes a safety microprocessor.

16. The infusion pump assembly of claim 13 wherein the one or more circuit partitioning components includes one or more of a diode assembly and a current limiting assembly.

17. The infusion pump assembly of claim 13 wherein the one or more circuit partitioning components are configured to allow the first battery to charge the super capacitor assembly by diverting a portion of the primary electrical energy from the at least a portion of the processing logic to the super capacitor assembly.

18. An infusion pump assembly comprising:
a reservoir assembly configured to contain an infusible fluid;
a motor assembly configured to dispense at least a portion of the infusible fluid contained within the reservoir assembly;
processing logic configured to control the motor assembly;
a primary power supply configured to provide primary electrical energy to at least a portion of the processing logic; and
a backup power supply configured to provide backup electrical energy to the at least a portion of the processing logic in the event that the primary power supply fails to provide the primary electrical energy to the at least a portion of the processing logic;
wherein the processing logic includes one or more circuit partitioning components configured to divide the processing logic into primary processing logic and backup processing logic.

19. The infusion pump assembly of claim 18 wherein the primary power supply includes a first battery.

20. The infusion pump assembly of claim 18 wherein the backup power supply is a super capacitor assembly.

21. The infusion pump assembly of claim 18 wherein the primary processing logic includes a primary microprocessor.

22. The infusion pump assembly of claim 18 wherein the one or more circuit partitioning components further configured to allow the primary power supply to charge the backup power supply by diverting a portion of the primary electrical energy from the at least a portion of the processing logic to the backup power supply.

23. The infusion pump assembly of claim 18 wherein the backup processing logic includes a safety microprocessor.

24. The infusion pump assembly of claim 18 wherein the one or more circuit partitioning components includes one or more of a diode assembly and a current limiting assembly.

25. The infusion pump assembly of claim 24 wherein the diode assembly is configured to allow the primary power supply to charge the backup power supply while prohibiting the backup power supply from providing backup electrical energy to the primary processing logic in the event that the primary power supply fails to provide the primary electrical energy to the primary processing logic.

* * * * *